United States Patent [19]

Straussberger et al.

[11] Patent Number: 5,777,146

[45] Date of Patent: Jul. 7, 1998

[54] PROCESS FOR PREPARING METHYLCHLOROSILANES

[75] Inventors: Herbert Straussberger; Willi Streckel; Bernd Pachaly, all of Mehring/Öd; Markus Reindl, Burghausen, all of Germany

[73] Assignee: Wacker-Chemie GmbH, Munich, Germany

[21] Appl. No.: 818,992

[22] Filed: Mar. 17, 1997

[30] Foreign Application Priority Data

May 30, 1996 [DE] Germany ............... 196 21 795.4

[51] Int. Cl.[6] ............................................. C07F 7/16
[52] U.S. Cl. ............................................. 556/472
[58] Field of Search ............................................. 556/472

[56] References Cited

U.S. PATENT DOCUMENTS

| | | |
|---|---|---|
| 2,380,997 | 8/1945 | Patnode . |
| 4,224,297 | 9/1980 | Straussberggr et al. . |
| 4,864,044 | 9/1989 | Lewis et al. . |
| 5,239,102 | 8/1993 | Webb et al. ............... 556/472 |
| 5,243,061 | 9/1993 | Webb et al. ............... 556/472 |

FOREIGN PATENT DOCUMENTS

| | | |
|---|---|---|
| 0440414 | 8/1991 | European Pat. Off. . |
| 2398020 | 2/1979 | France . |
| 2933342 | 3/1981 | Germany . |

OTHER PUBLICATIONS

H. Lieske et al., Silicon for Chemical Industry, Geiranger-Norway, Jun. 18, 1992 Characterization of Rochow Contact Masses by Catalytic Results, XRD, Chemisorption and XPS.

Derwent Abstract corresponding to DE 29 33 342 A1 (#8A-23532D).

*Primary Examiner*—Paul F. Shaver
*Attorney, Agent, or Firm*—Brooks & Kushman

[57] ABSTRACT

In a process for the direct synthesis of methylchlorosilanes by reacting methyl chloride with a catalytic composition comprising silicon, copper catalyst and promoters, where at least some of the catalytic composition is comprised of the catalytic composition from a prior production campaign.

11 Claims, No Drawings

PROCESS FOR PREPARING METHYLCHLOROSILANES

BACKGROUND OF THE INVENTION

The present invention relates to a process for the direct synthesis of methylchlorosilanes by the Müller-Rochow method, in which catalytic composition collected during a production campaign is added.

In the Müller-Rochow direct synthesis, methyl chloride and silicon are reacted in the presence of a copper catalyst and suitable promoters to give methylchlorosilanes. The direct synthesis is the only significant production process for the monomeric starting materials for polysiloxanes. The most important target product of the direct synthesis is dimethyldichlorosilane.

Despite the economic importance of the direct synthesis, some of the scientific background has not been explored. According to H. Lieske et al. in Silicon for Chemical Industry, Geiranger-Norway, Jun. 16–18, 1992, the reproducibility of the experiments is often poor owing to the participation of three solids in the reaction, namely silicon, catalyst and promoters. In practice, different batches in the direct synthesis give different results despite the same material and reaction parameters.

The direct synthesis can be carried out batchwise or continuously. In industrial production only the continuous embodiment is used. The continuous direct synthesis is carried out in fluidized-bed reactors in which methyl chloride is used simultaneously as fluidizing medium and reactant. The silicon required is previously milled to a powder having a particle size of from 25 to 500 µm and mixed with copper catalyst and promoters to give the catalytic composition.

During continuous operation of a reactor, the production rate based on methylchlorosilanes and the selectivity of the direct synthesis process in respect of the target product dimethyldichlorosilane decrease after a largely stable production phase. For this reason, the production campaign has to be stopped after a certain time. A production campaign therefore usually lasts for only a few days to a number of weeks.

After the end of a production campaign, the reactor is emptied, recharged with silicon, copper catalyst and promoters and again brought to the reaction conditions. Only after a certain time of activation, which is referred to as the start phase, does the reactor reach the stable production phase. In the start phase, selectivity and production rate are significantly reduced. The reactor therefore does not operate economically in the start phase.

In the start phase, the catalytic composition has to be activated. This activation is generally carried out in situ, i.e. in the reactor in which the direct synthesis is also carried out, using methyl chloride.

Activation with another gas is known. U.S. Pat. No. 2,380,997 describes a process for activating a catalytic composition by heating with hydrogen. Activation using hydrogen chloride is known from U.S. Pat. No. 4,864,044. The significant advantage of this external activation is the shortening of the induction time at the beginning of a production campaign. The induction time is the period in which active reaction centers form on the surface of the silicon until finally the formation of methylchlorosilanes commences. Activation using hydrogen chloride has the disadvantage that some metals added as promoters are carried away from the catalytic composition and selectivity and production rate thus become less favorable.

Activation of the catalytic composition with a different gas requires a great amount of time. This activation is therefore practical only if it is carried out externally in a separate reactor. In this case, the activated catalytic composition is usually transferred pneumatically under inert conditions into the reactor.

However, the advantages of external activation are more than counteracted by the disadvantage that it requires an additional process step and the complex plant engineering necessary for this, plus additional reactor times. For these reasons, external activation has not been established in the process technology which is customary at present.

EP-A-440 414 describes a process for the external activation of a catalytic composition using methyl chloride. The activated catalytic composition is cooled and stored. However, since the productivity and selectivity based on dimethyldichlorosilane of the activated compositions fluctuate greatly, poorer activated catalytic compositions either have to be used regardless or discarded.

BRIEF SUMMARY OF THE INVENTION

It is an object of the present invention to provide a process for the direct synthesis of methylchlorosilanes by the Müller-Rochow method, which has a short running-up phase and in which productivity and selectivity based on dimethyldichlorosilane can be controlled without having to discard the catalytic composition.

DETAILED DESCRIPTION OF THE INVENTION

The present invention provides a process for the direct synthesis of methylchlorosilanes by reacting methyl chloride with a catalytic composition comprising silicon, copper catalyst and promoters, wherein the catalytic composition collected during a production campaign is added.

The catalytic composition of a production campaign remains active for a number of months if it is stored with exclusion of oxygen and achieves the previously shown selectivity and reactivity when it is used in a production campaign. Collecting a catalytic composition from a production campaign having known process parameters and adding this catalytic composition to a production campaign enables the course of the latter to be influenced in a targeted way. This enables the reactor to be operated optimally.

Preference is given to collecting a catalytic composition in a production campaign which is comparatively good in respect of selectivity and reactivity. The reactivity is based on the sum of the methylchlorosilanes formed and the selectivity is based on the most important target products, in particular dimethyldichlorosilane.

The catalytic composition collected, optionally in admixture with fresh catalytic composition, is preferably initially charged at the start of a new production campaign. The start phase of the production campaign is then shortened. Both the induction time, i.e. the time from the start to the commencement of silane formation, and also the subsequent initial phase in which a crude silane mixture is produced are reduced.

Mixing in a catalytic composition which has been collected from a production campaign which was comparatively good in respect of selectivity and reactivity gives better selectivity and reactivity than if the catalytic composition were activated with hydrogen chloride.

Compared with the external activation of the catalytic composition, the present process requires only an additional collection container for catalytic composition to be used in industrial practice.

The catalytic composition collected is used in an amount of at least 5% by weight, preferably at least 10% by weight, more preferably at least 20% by weight, based on the total amount of catalytic composition used. The remainder then consists of fresh catalytic composition which is prepared from silicon, copper catalyst and promoters. At the start of a new production campaign, the catalytic composition can also comprise up to 100% by weight of collected catalytic composition. Preference is given to using at most 90% by weight, more preferably 50% by weight, of collected catalytic composition.

In the process, further previously collected catalytic composition, optionally together with fresh catalytic composition, can also be added during the production phase of a production campaign. The catalytic composition added is collected in a phase in which the selectivity and reactivity are good. This enables selectivity and reactivity in the production phase to be increased when these parameters, for example, become poorer. The running time of a campaign can be increased in this way. The catalytic composition added can be collected during a previous production campaign or in a previous phase of the same production campaign.

The amounts of catalytic composition added correspond to the amounts of collected catalytic composition added at the start of a new production campaign.

The catalytic composition collected from a production campaign is stored under nitrogen, argon, methyl chloride or hydrogen.

In the following examples, unless otherwise indicated, a) all amounts are by weight;

b) all pressures are 0.10 Mpa (abs.);

c) all temperatures are 20° C.

d) silane HM2=dimethylchlorosilane
silane HM=methyldichlorosilane
silane M1=methyltrichlorosilane
silane M2=dimethyldichlorosilane
silane M3=trimethylchlorosilane

EXAMPLES

Example 1 describes the customary embodiment with in situ activation. Example 2 describes external activation with hydrogen chloride using the same ratios of silicon: copper catalyst: promoters. Example 3 a-c describes the mixing in of activated catalytic composition in amounts of 25%, 50% and 75%. The following are used to evaluate the results:

a) the induction time, i.e. the time from the start to the commencement of silane formation, b) the formation times for 5×10 ml of crude silane, i.e. the production rates in the initial phase until the stable production phase is reached, c) the crude silane composition, especially content of undesired silane HM and desired target product silane M2, d) the elemental composition of the reaction mass after formation of the 5×10 ml of crude silane, i.e. reaching the concentrations customary in the in situ activation, also when activated catalytic composition is mixed in.

Mixing in activated catalytic composition gives, compared with in situ activation, a significantly reduced induction time, a significantly better production rate, a better selectivity and the same composition of the reaction mass. In the comparative example, external activation using hydrogen chloride gives significantly poorer results with the exception of a reduced induction time. Even if the same improvement in results as for the mixing in according to the invention of activated catalytic composition is assumed for the external activation using hydrogen chloride, there remains the disadvantage of an additional process step and complicated process technology. Example 1

In a standardized test procedure, silicon was reacted with chloromethane in the presence of a copper catalyst to give methylchlorosilanes. A laboratory fluidized-bed reactor having an internal diameter of 25 mm and provided with a heating winding, a gas distribution frit, an internal thermometer, a distillation attachment with brine cooling and a graduated receiver was used for this purpose. 120 g of silicon powder having a particle size of 70–240 μm mixed with 6 g of copper(II) oxide, 1 g of zinc oxide and 6 mg of tin powder were initially charged. The mixture was heated under 40 l/h of nitrogen and when an internal temperature of 350° C. had been reached, the nitrogen was replaced by 40 l/h of chloromethane. The time to the formation of the crude silane mixture (induc-tion time) was measured. 5×10 ml of crude silane mixture were then collected by changing the receiver, the formation times of each 10 ml were measured and the samples collected were analyzed by gas chromatography. After formation of 50 ml of crude silane mixture (corresponding to a silicon conversion of about 10%), the experiment was stopped. An elemental analysis was carried out on the catalytic composition remaining in the reactor. The test procedure was carried out twice. The activated catalytic composition was collected and stored at 20° C. under nitrogen. The average values of the two test runs are shown below.

| Crude silane fraction | Formation time (minutes) | Silane HM2 (%) | Silane HM (%) | Silane M3 (%) | Silane M1 (%) | Silane M2 (%) |
|---|---|---|---|---|---|---|
| | | Induction Time 24 Minutes | | | | |
| 10 ml | 19 | 0.31 | 3.80 | 3.85 | 7.58 | 84.31 |
| 20 ml | 19.5 | 0.30 | 2.14 | 2.11 | 5.21 | 90.24 |
| 30 ml | 19.5 | 0.33 | 1.72 | 1.90 | 4.35 | 91.70 |
| 40 ml | 19.5 | 0.31 | 1.53 | 1.76 | 4.26 | 92.14 |
| 50 ml | 22 | 0.38 | 1.56 | 1.79 | 3.94 | 92.34 |

| Analysis of the reaction mass: | | | | | | |
|---|---|---|---|---|---|---|
| Element | Al | Ca | Fe | Cu | Zn | Sn |
| Content (%) | 0.11 | 0.022 | 0.28 | 1.35 | 0.213 | 0.0014 |

Example 2

Direct synthesis with external activation using hydrogen chloride (not according to the invention)

The standardized test procedure as described in Example 1 was repeated, but, as a change from Example 1, the mixture was heated under 40 l/h of nitrogen and when an internal temperature of 350° C. was attained, the nitrogen was replaced by 40 l/h of hydrogen chloride and the mixture was heated until silane mixture was formed. Subsequently, it was cooled under 40 l/h of nitrogen, the catalytic composition was transferred under inert conditions into another reactor and the test was commenced as with fresh catalytic composition as described in Example 1. The time to the formation of the crude silane mixture was measured (induction time).

| | | Induction Time 16 Minutes | | | | |
|---|---|---|---|---|---|---|
| Crude silane fraction | Formation time (minutes) | Silane HM2 (%) | Silane HM (%) | Silane M3 (%) | Silane M1 (%) | Silane M2 (%) |
| 10 ml | 109 | 0.05 | 0.92 | 5.33 | 20.13 | 73.56 |
| 20 ml | 87 | 0.04 | 1.44 | 5.12 | 15.09 | 78.32 |
| 30 ml | — | — | — | — | — | — |
| 40 ml | — | — | — | — | — | — |
| 50 ml | — | — | — | — | — | — |

Owing to the poor production rate, the test was stopped after formation of 20 ml of crude silane

| | Analysis of the reaction mass: | | | | | |
|---|---|---|---|---|---|---|
| Element | Al | Ca | Fe | Cu | Zn | Sn |
| Content (%) | 0.07 | 0.025 | 0.27 | 3.65 | 0.514 | 0.0003 |

The high concentration of Cu and Zn and the low concentration of Al and Sn compared with Example 1 can clearly be seen.

Example 3

Direct synthesis with mixing in of collected catalytic composition (according to the invention)

The collected catalytic composition from Example 1 was mixed in ratios of 75:25, 50:50 and 25:75 with fresh catalytic composition under inert conditions and the test was commenced as with fresh catalytic composition as described in Example 1. The time to the formation of the crude silane mixture was measured (induction time).

Example 3 a

Mixing in of 25% of collected catalytic composition

| | | Induction Time 19 Minutes | | | | |
|---|---|---|---|---|---|---|
| Crude silane fraction | Formation time (minutes) | Silane HM2 (%) | Silane HM (%) | Silane M3 (%) | Silane M1 (%) | Silane M2 (%) |
| 10 ml | 20 | 0.60 | 3.44 | 4.95 | 11.60 | 79.40 |
| 20 ml | 18 | 0.36 | 1.65 | 3.14 | 6.59 | 88.25 |
| 30 ml | 17 | 0.29 | 0.95 | 2.92 | 5.43 | 90.41 |
| 40 ml | 15 | 0.27 | 0.82 | 2.92 | 5.22 | 90.77 |
| 50 ml | 14 | 0.25 | 0.84 | 2.69 | 5.23 | 91.00 |

| | Analysis of the reaction mass: | | | | | |
|---|---|---|---|---|---|---|
| Element | Al | Ca | Fe | Cu | Zn | Sn |
| Content (%) | 0.11 | 0.024 | 0.28 | 1.20 | 0.258 | 0.0024 |

Example 3 b

Mixing in of 50% of collected catalytic composition

| | | Induction Time 13 Minutes | | | | |
|---|---|---|---|---|---|---|
| Crude silane fraction | Formation time (minutes) | Silane HM2 (%) | Silane HM (%) | Silane M3 (%) | Silane M1 (%) | Silane M2 (%) |
| 10 ml | 29 | 0.76 | 2.84 | 4.23 | 10.04 | 82.11 |
| 20 ml | 18 | 0.44 | 1.33 | 3.16 | 6.14 | 88.94 |
| 30 ml | 18 | 0.36 | 0.90 | 3.20 | 5.64 | 89.90 |
| 40 ml | 19 | 0.30 | 0.74 | 3.14 | 5.35 | 90.47 |
| 50 ml | 17 | 0.29 | 0.68 | 3.18 | 5.30 | 90.55 |

| | Analysis of the reaction mass: | | | | | |
|---|---|---|---|---|---|---|
| Element | Al | Ca | Fe | Cu | Zn | Sn |
| Content (%) | 0.12 | 0.027 | 0.30 | 1.40 | 0.290 | 0.0028 |

Example 3 c

Mixing in of 75% of collected catalytic composition

| | | Induction Time 8 Minutes | | | | |
|---|---|---|---|---|---|---|
| Crude silane fraction | Formation time (minutes) | Silane HM2 (%) | Silane HM (%) | Silane M3 (%) | Silane M1 (%) | Silane M2 (%) |
| 10 ml | 12 | 0.79 | 4.83 | 4.12 | 11.34 | 78.92 |
| 20 ml | 17 | 0.47 | 1.93 | 2.45 | 5.24 | 89.91 |
| 30 ml | 16 | 0.40 | 1.27 | 2.60 | 4.91 | 90.81 |
| 40 ml | 17 | 0.38 | 1.15 | 2.60 | 4.76 | 91.12 |
| 50 ml | 15 | 0.35 | 1.00 | 2.69 | 4.81 | 91.15 |

| | Analysis of the reaction mass: | | | | | |
|---|---|---|---|---|---|---|
| Element | Al | Ca | Fe | Cu | Zn | Sn |
| Content (%) | 0.13 | 0.025 | 0.29 | 1.42 | 0.228 | 0.0019 |

What is claimed is:

1. A process for direct synthesis of methylchlorosilanes, comprising reacting methyl chloride with a catalytic composition comprising silicon, copper catalyst and promoters, wherein at least 5% by weight of the catalytic composition based on the total weight of the catalytic composition, comprises a catalytic composition of known activity from a previous production campaign which has been stored to the exclusion of oxygen such that its activity is retained.

2. The process as claimed in claim 1, wherein the catalytic composition is from a production campaign which has high selectivity in respect of dimethyldichlorosilane and high reactivity based on the amount of methylchlorosilanes formed.

3. The process as claimed in claim 1, wherein the catalytic composition from a production campaign, optionally in admixture with fresh catalytic composition, is charged at the start of a new production campaign.

4. The process as claimed in claim 1, wherein the catalytic composition from a production campaign, optionally together with fresh catalytic composition, is added during the production phase of the process.

5. The process as claimed in claim 1, wherein a mixture comprising from 10% to 90% by weight of the catalytic composition from a production campaign is present.

6. The process as claimed in claim 1, wherein the catalytic composition from a production campaign is stored under nitrogen, argon, methyl chloride or hydrogen prior to addition of the direct synthesis.

7. A process for reducing the induction period during the direct method synthesis of methylchlorosilanes in the presence of a direct method catalytic composition comprising silicon, copper, and promoters, said process comprising:

a) collecting a prior catalytic composition exhibiting good reactivity and selectivity from the production phase of a previous direct synthesis which has been stored such that its catalytic activity is retained;

b) adding at least 5 weight percent of the catalyst collected in step a) to fresh direct method catalyst, and c) reacting methylchloride in the presence of said mixture of a) and b)

such that the induction period of the combination of said prior catalytic composition and said fresh direct method catalyst is less than that obtained when using fresh direct method catalyst alone.

8. The process of claim 7 wherein additional prior catalytic composition is added during a production phase of methylchlorosilane synthesis.

9. A process for the preparation of methylchlorosilanes by the direct method, comprising reacting methylchloride in the presence of a catalytic composition comprising a fresh direct method catalyst comprising silicon, copper, and promoters, and admixed therewith at least 5 weight percent, based on total catalyst composition, of a prior catalytic composition derived from a prior direct method synthesis having a catalytic activity known from said prior direct method synthesis, and not having been thermally treated at elevated temperature.

10. The process of claim 9 wherein said prior catalyst composition has been maintained to the exclusion of oxygen.

11. The process of claim 9 wherein said prior catalyst composition has been maintained at ambient temperature.

\* \* \* \* \*